United States Patent
Cavazza

(10) Patent No.: US 6,245,378 B1
(45) Date of Patent: Jun. 12, 2001

(54) NUTRITIONAL SUPPLEMENT FOR FACILITATING SKELETAL MUSCLE ADAPTATION TO STRENUOUS EXERCISE AND COUNTERACTING DEFATIGATION IN ASTHENIC INDIVIDUALS

(75) Inventor: Claudio Cavazza, Rome (IT)

(73) Assignee: Sigma-Tau Healthscience S.p.A., Pomezia (IT)

( * ) Notice: Subject to any disclaimer, the term of this patent is extended or adjusted under 35 U.S.C. 154(b) by 0 days.

(21) Appl. No.: 09/147,179

(22) PCT Filed: Mar. 27, 1998

(86) PCT No.: PCT/IT98/00069

§ 371 Date: Nov. 30, 1998

§ 102(e) Date: Nov. 30, 1998

(87) PCT Pub. No.: WO98/43499

PCT Pub. Date: Oct. 8, 1998

(30) Foreign Application Priority Data

Apr. 1, 1997 (IT) .............................................. RM97A0185

(51) Int. Cl.$^7$ ................................................. A01K 31/205
(52) U.S. Cl. .................. 426/656; 426/800; 426/806; 426/72; 426/439; 424/439
(58) Field of Search ..................... 426/656, 300, 426/806, 72; 424/439

(56) References Cited

U.S. PATENT DOCUMENTS

| | | | |
|---|---|---|---|
| 4,194,006 | * 3/1980 | Cavazza | 424/311 |
| 4,254,147 | * 3/1981 | Cavazza | 426/656 |
| 4,255,449 | * 3/1981 | Cavazza | 426/656 |
| 4,267,194 | * 5/1981 | Durlach | 424/315 |
| 4,315,944 | * 2/1982 | Ramacci | 424/319 |
| 4,320,145 | * 3/1982 | Cavazza | 426/656 |
| 4,343,816 | * 8/1982 | Cavazza | 424/316 |
| 4,346,107 | 8/1982 | Cavazza et al. | 424/316 |
| 4,400,371 | * 8/1983 | De Felice | 424/10 |
| 4,415,589 | 11/1983 | Cavazza | 424/311 |
| 4,474,812 | * 10/1984 | Cavazza | 424/319 |
| 4,599,232 | * 7/1986 | Bertelli | 424/94 |
| 4,602,039 | * 7/1986 | Cavazza | 514/561 |
| 4,604,286 | * 8/1986 | Kawajiri | 424/149 |
| 4,649,159 | * 3/1987 | Fanelli | 514/556 |
| 4,656,191 | * 4/1987 | Fanelli | 514/556 |
| 4,713,379 | * 12/1987 | Kramer et al. | 514/212 |
| 4,751,242 | * 6/1988 | Calvani et al. | 514/554 |
| 5,227,518 | * 7/1993 | Cavazza | 560/253 |
| 5,631,288 | 5/1997 | De Simone | 514/556 |
| 5,817,329 | * 10/1998 | Gardiner | 424/439 |

FOREIGN PATENT DOCUMENTS

WO 88/01861  3/1988 (WO) .

OTHER PUBLICATIONS

Williamson et al., Hyperglycemic Pseudohypoxia and Diabetic Complications. Diabetes., v 42, n6, p. 801(3), Jun. 1993.*

Murray, F. Learn to Improve Your Health With Amino Acids., Better Nutrition For Today's Living., v57 n7, p66–71, Jul. 1995.*

Sugiyama et al., Mechanism of Free Fatty–Acid Induced Arrhythmias., Journal of Electrocardiology., 15 (3). 227–232, 1982.*

* cited by examiner

*Primary Examiner*—Keith Hendricks
*Assistant Examiner*—Philip DuBois
(74) *Attorney, Agent, or Firm*—Oblon, Spivak, McClelland, Maier & Neustadt, P.C.

(57) ABSTRACT

A nutritional supplement for facilitating the adaptation of skeletal muscle in individuals udergoing programs of strenuous exercise and counteracting defatigation and weariness in asthenic individuals is disclosed, which comprises a combination of L-camitine, acetyl L-camitine and propionyl L-carnitine as basic active ingredients. Optional ingredients comprise isovaleryl L-carnitine, branched-chained aminoacids and creatine and/or phosphocreatine.

14 Claims, No Drawings

NUTRITIONAL SUPPLEMENT FOR FACILITATING SKELETAL MUSCLE ADAPTATION TO STRENUOUS EXERCISE AND COUNTERACTING DEFATIGATION IN ASTHENIC INDIVIDUALS

This application is a 371 application of PCT/IT98/00069 filed on Mar. 27, 1998.

The present invention relates to a nutritional supplement comprising a combination of "carnitines" as the basic active ingredients, where what is meant by "carnitines" are L-carnitine and the first terms of the series of lower (short-chain) acyl L-carnitines, or their pharmacologically acceptable salts.

This nutritional supplement is particularly suitable both for modulating the adaptation of skeletal muscle and of the liver in individuals who engage in intense, prolonged physical activity and for combating the sensation of muscular fatigue and weariness presented by asthenic subjects even in the absence of any type of more or less intense physical activity.

Anyone who engages in sporting activity, whether as a professional or as an amateur, wishes to achieve the maximum degree of adapation of the -skeletal muscles to the ability to support prolonged periods of intense physical effort in a short space of time and then maintain it for as long as possible. The quest for this optimal degree of physical fitness may make for the abuse of drugs, particularly steroids. It is well known that such drugs can increase protein synthesis and consequently enhance the growth of muscle mass to a greater extent than could be achieved by training and diet. The use of such drugs, however, is unquestionably harmful as well as being illegal when practised in the sphere of professional sport.

It is therefore clear that the only way to achieve the above-mentioned objective correctly consists in undergoing appropriate training schedules in combination with suitable diets, enhanced with suitable nutritional supplements. What is meant by asthenia is that diffuse set of a specific symptoms typical of the present-day stressful conditions of life particularly prevalent in the large urban conurbations and affecting a vast population, largely regardless of factors related to age and social condition, and characterised by a lack of loss of muscular strength, weariness, with easy fatigability and an inadequate reaction to stimuli.

The object of the present invention is to provide a nutritional supplement which is useful for both the above-mentioned categories of consumers.

Over the decades which have now elapsed since the fundamental discovery (Fritz I. B.: The metabolic consequences of the effects of carnitine on long-chain fatty acid oxidation. In Cellular Compartmentalization and Control of Fatty Acid Metabolism. Edited by F. C. Gran, New York, Academic Press, 1968, pp. 39–63) that L-carnitine is unique in performing a vital physiological role as the carrier of long-chain fatty acid across the internal mitochondrial membrane into the mitochondrial matrix, the sit of their oxidation, and since it was first established (Engel and Angelini, Science, 1973, 179: 899–902) that a primary deficiency of L-carnitine is the cause of a severe and sometimes fatal, though rare, form of myopathy (lipid storage myopathy), our knowledge of the pathological consequences of primary and secondary L-carnitine deficiencies and, conversely, of the therapeutic and nutritional value of an exogenous supply of carnitine has increased enormously.

Carnitine is present in all biological tissues in relatively high concentrations as free carnitine and in lower concentrations in the form of acyl carnitines which are metabolic products of the reversible reactions:

acyl CoA+carnitine⇌acyl carnitine+CoASH catalysed by three groups of enzymes, the transferases, which distinguish themselves mainly by their specificity for reactive substrates: the group of carnitine acetyl transferase (CAT) which have as their substrate the short-chain acyl groups (such as acetyl and propionyl), the group of carnitine octanoyl transferases (COT) which have as their substrate the medium-chain acyl groups and the group of carnitine palmitoyl transferases (CPT) which have as their substrate the long-chain acyl groups.

The important role of carnitine in intermediate metabolism, particularly in terms of its limited biosynthesis, serves to explain how a carnitine deficiency can occur as a secondary event in various pathological functions, involving different organs and apparatuses. The broadening of the clinical spectrum has been accompanied by a growing number of therapeutic opportunities related to the efficacy of this naturally occurring compound: efficacy which has revealed itself in all its potential with the observation that replacement therapy with L-carnitine reverses the dramatic clinical picture in patients suffering from lipid storage myopathy. The US Food and Drug Administration (FDA) has not only accorded L-carnitine the status of an orphan drug, but has also included it in the list of life-saving drugs.

Parallel to our deeper insight into the pathological implications related to primary and secondary carnitine deficiency there has been an impressive build-up of scientific and patent publications focusing mainly on L-carnitine and, to a substantially lesser extent, on a number of acyl carnitines.

Confining ourselves to a partial review of the picture, the use of L-carnitine has been proposed in the cardiovascular field for the treatment of cardiac arrhythmias and congestive heart failure (U.S. Pat. No. 4,656,191), of myocardial ischaemia and anoxia (U.S. Pat. No. 4,649,159); in the field of lipid metabolism disorders, for the treatment of hyperlipidaemia and hyperlipoproteinaemias (U.S. Pat. No. 4,315, 944) and for normalising an abnormal ratio of HDL to LDL+VLDL (U.S. Pat. No. 4.255,449); in the field of total parenteral nutrition (U.S. Pat. Nos. 4,254,147 and 4,320, 145); in nephrology, for combating myasthenia and the onset of muscle cramps caused by the loss of carnitine in dialysis fluid in chronic uraemic patients under regular haemodialysis treatment (U.S. Pat. No. 4,272,549); for counteracting the toxic effects induced by anticancer agents such as Adriamycin (U.S. Pat. Nos. 4,400,371 and 4,713,379) and by halogen-containing anaesthetics such as halotane (U.S. Pat. No. 4,780,308); in the treatment of venous stasis (U.S. Pat. No. 4,415,589); for counteracting the deterioration of a number of biochemical and behavioural parameters in elderly subjects (U.S. Pat. No. 4,474,812); for normalising triglyceride and Tumor Necrosis Factor (TNF) levels in patients suffering from AIDS and asymptomatic HIV-seropositive patients (U.S. Pat. No. 5,631,288).

The use of L-carnitine has also been proposed in combination with other active ingredients, as in the combination of L-carnitine plus coenzyme Q10 with a broad spectrum of metabolic/antiatherosclerotic activity (U.S. Pat. No. 4,599, 232).

As regards the acyl carnitines, the use of acetyl L-carnitine is well known for the treatment of diseases of the central nervous system, particularly Alzheimer disease (U.S. Pat. No. 4,346,107), and for the treatment of diabetic neuropathy (U.S. Pat. No. 4,751,242), while propionyl L-carnitine has been proposed for the treatment of peripheral vascular disease (U.S. Pat. No. 4,343,816) and congestive heart failure (U.S. Pat. No. 4,194,006).

One thing which clearly emerges from the patent picture outlined here above, albeit in a concise and partial manner, is the distinctly greater weight and importance of L-carnitine compared to its acyl derivatives.

An analysis of the patent literature reveals that, in certain circumstances, mention is made of an equivalence of behaviour between L-carnitine and some of the lower acyl carnitines with regard to a given indication, an equivalence which, on closer inspection, is found to stem more from patent motivations aimed at obtaining the broadest protection possible than from the results of appropriate pharmacological/clinical research. This "equivalence" of behaviour is probably also suggested by the above-mentioned reversible equilibrium reaction between carnitine and the acyl carnitines.

From an examination of the scientific and patent literature it also emerges tat the attention of researchers has been constantly focused specifically on the individual carnitines and, as already mentioned, mainly on L-carnitine, which has created a kind of single-compound culture which in actual fact is a technical prejudice which has hindered investigations into the efficacy of mixtures of "carnitines". There is no evidence, in fact, that a combination containing a mixture of L-carnitine, acetyl L-carnitine and propionyl L-carnitine (or their pharmacologically acceptable salts) as basic active ingredients has ever been proposed for therapeutic or nutritional purposes. Obviously, there has never been any previous disclosure of such a combination in which L-carnitine, acetyl L-carnitine and propionyl L-carnitine are present in clearly determined weight-to-weight ratios (as will be described in detail here below), such weight-to-weight ratios being critical with a view to achieving the desired therapeutic/nutritional effects.

It has now been found that the combination of L-carnitine, acetyl L-carnitine and propionyl L-carnitine (or their pharmacologically acceptable salts) exerts an unexpected potent synergic effect as compared to the single "carnitines", as demonstrated by various tests in which the effect of the combination has been compared with that of L-carnitine, acetyl L-carnitine and propionyl L-carnitine when administered alone.

That the combined action of the three "carnitines" may affect both the fatty acid glycolytic and oxidative pathways is not surprising. Moreover, the presence of propionyl L-carnitine, a substance capable of fuelling the Krebs cycle at succinyl-CoA level (anaplerotic action), increases its overall velocity. It is clear that this increase in velocity may be facilitated by an adequate supply of acetyl units. This latter action is accomplished by acetyl L-carnitine. In point of fact, thanks to the presence of mitochondrial carnitine acetyl transferases, the acetyl groups of acetyl L-carnitine may be transferred to CoA for the purposes of synthesising acetyl-CoA, a key compound in the Krebs cycle. Lastly, carnitine, through its well-known action on the transfer of fatty acids into the mitochondrial matrix, enhances the oxidation of the fatty acids themselves, the latter being the compounds from which the muscles extracts most of the energy needed for the contraction process.

These obvious considerations, however, would have led one to expect at most an "additive" effect of the combination of "carnitine" and not the surprising remarkable synergic effect marked by an enhanced rate of ATP output, the cell main energy source, shown by the clinical studies which will be given in detail here below.

As a result of the studies which have made it possible to identified this synergic effect, the present invention provides a nutritional supplement which comprises the following combination:

(a) L-carnitine;
(b) Acetyl L-carnitine;
(c) Propionyl L-carnitine,
or their pharmacologically acceptable salts; and
a pharmacologically acceptable excipient.

The weight-to-weight ratio (a):(b):(c) ranges from 1:1:1 to 1:0.1:0.1, where the aforementioned weight-to-weight ratios refer to L-carnitine, acetyl L-carnitine and propionyl L-carnitine expressed as inner salts.

It has also been found that, in addition to the essential ingredients of the combination (L-carnitine, acetyl L-carnitine and propionyl L-carnitine or their pharmacologically acceptable salts), the nutritional supplement of the invention may also advantageously comprise an additional acyl L-carnitine, such as isovaleryl L-carnitine, a mixture of essential amino acids and creatine and/or phosphocreatine.

The weight-to-weight ratio between L-carnitine, acetyl L-carnitine, propionyl L-carnitine and isovaleryl L-carnitine ranges from 1:1:1:1 to 1:01:01:01 and is preferably 1:0,5:0,5:0,5.

All the amino acids, whether essential or non-essential, are substrates needed by the muscle cells for protein synthesis. It is known that the amino acids in excess of those required for the synthesis of proteins and other macromolecules can be neither excreted nor stored, unlike the case of fatty acids and glucose. The excess amino acids, on the other hand, are used as energy material. Whereas the α-amino groups are removed, the carbon atom skeleton that remains is converted into fundamental metabolic intermediate products. Most of the amino groups of the excess amino acids are transformed into urea, whereas the carbon skeleton is converted to acetyl CoA, acetoacetyl CoA, pyruvate, or to one of the intermediate products of the citric acid cycle. Fatty acids, ketone bodies and glucose can thus be formed from the amino acids.

Preferably, the essential amino acid mixture consists of the branched-chain amino acids valine, leucine and isoleucine.

The nutritional supplement of the invention may advantageously also comprise non-essential amino acids, particularly glutamine, L-glutamic acid, L-aspartic acid and L-asparagine.

An example of the nutritional supplement of the invention comprises:

(i) from 40 to 60% by weight of a mixture of L-carnitine, acetyl L-carnitine, propionyl L-carnitine, or their pharmacologically acceptable salts;

(ii) from 10 to 15% by weight of valine; from 10 to 15% by weight of leucine; from 10 to 15% by weight of isoleucine; and (iii) from 8 to 12% by weight of creatine or phosphocreatine.

If non-essential amino acids are present, the nutritional supplement will also comprise from 10 to 30% by weight of such amino acids.

To all the effects and purposes of the present invention, what is meant by L-carnitine, acetyl L-carnitine, propionyl L-carnitine and isovaleryl L-carnitine are these compounds in the form of inner salts.

What is meant by pharmacologically acceptable salt of L-carnitine, acetyl L-carnitine, propionyl L-carnitine or isovaleryl L-carnitine is any salt of these with an acid that does not give rise to unwanted toxic or side effects. These acids are well known to pharmacologists and to experts in pharmacy.

Non-limiting examples of such salts are: chloride; bromide; iodide; aspartate; acid aspartate; citrate; acid citrate;

tartrate; phosphate; acid phosphate; fumarate; acid fumarate; glycerophosphate; glucose phosphate; lactate; maleate; acid maleate; orotate; oxalate; acid oxalate; sulphate; acid sulphate; trichloroacetate; trifluoroacetate and methanesulphonate.

A list of FDA-approved pharmacologically acceptable salts is given in Int. J. of Pharm. 33, (1986), 201–217; this latter publication is incorporated herein by reference.

Fumarate is particularly preferred in that, for example, L-carnitine fumarate exerts a double protective action on protein metabolism; through a direct increase in intermediate metabolism, it indirectly stimulates the biosynthesis of proteins and, as a result of the mobilisation of fatty acids, it induces a sparing/protective effect on the components of muscle protein.

Towards both those individuals undergoing programs of strenuous exercise and the asthenic individuals, the best results are obtained following the administration of about 500 mg/day of L-carnitine, 50–500 mg/day of acetyl L-carnitine and 50–500 mg/day of propionyl L-carnitine or an equivalent amount by weight of a pharmacologically acceptable salt thereof.

The nutritional supplement may also contain mineral salts such as, for instance, disodium citrate, monopotassium phosphate, calcium lactate and magnesium taurinate.

The nutritional supplement of the invention is suitable for oral intake.

The nutritional supplement must not be used as the only or main source of nutrition on a day-to-day basis.

The complementary part of the diet will therefore consist in the appropriate amino acids, carbohydrates, fats, vitamins and mineral substances.

The amount of the nutritional supplement to be taken daily may vary within broad limits, depending, for example, on the subject's age and body weight, as well as on the intensity and complexity of the training schedule or, as the case may be, the physical activity the subject engages in. Generally speaking, however, the amount of proteins ingested with the nutritional supplement will not exceed 30–35% by weight of the overall amount of proteins normally ingested by the subject daily.

The rational, prolonged use of the nutritional supplement of the invention enables the following positive effects to be achieved:

(a) conservation of the muscle proteins and particularly the branched-chain amino acids present in skeletal muscle;

(b) stimulation of protein synthesis in skeletal muscle and in the liver;

(c) making available amino groups for the synthesis of alanine and glutamine, both of which take part in gluconeogenesis;

(d) facilitation of the metabolic conversion of pyruvate to alanine rather than lactate; and (e) facilitation of the afflux of hydrogen ions from skeletal muscle via the conversion of glutamate to glutamine to maintain an optimal intramuscular pH value.

A non-limiting example of the nutritional supplement of the invention is given here below. This composition is suitable for oral intake in liquid form, after being appropriately dissolved in a sufficient volume of water, e.g. 200–300 mL.

| Basic Active ingredients | daily dose |
|---|---|
| L-carnitine fumarate | 200 mg |
| (= 143 mg L-carnitine inner salt) | |
| Acetyl L-carnitine | 75 mg |
| Propionyl L-carnitine | 75 mg |
| Branched-chain amino acids and non-essential amino acids | |
| Isoleucine | 50 mg |
| Leucine | 50 mg |
| Valine | 50 mg |
| Aspartic acid | 150 mg |
| Glutamic acid | 200 mg |
| Asparagine | 100 mg |
| Fosfocreatine | 50 mg |
| Vitamins | |
| Vitamin C | 250 mg |
| Mineral salts | |
| Disodium citrate (= 7,8 mg Na) | 40 mg |
| Monopotassium phosphate (= 8,6 mg K) | 30 mg |
| Calcium lactate (= 20 mg Ca) | 110 mg |
| Magnesium taurinate (= 73,0 mg Mg) | 820 mg |
| Total amount of active ingredients | 2250 mg |
| Excipients | 2750 mg |
| Total weight | 5000 mg |

It will be apparent to any expert in pharmacy that by means of the use of suitable excipients the compositions of the present invention can be formulated in solid form, so as to be taken in the form of tablets, chewable tablets, capsules or the like.

A number of studies are given here below which demonstrate the synergic effect of the combination of L-carnitine, acetyl L-carnitine and propionyl L-carnitine as compared to the single constituents alone.

Effect of the Combination on Exercise Performance

Two studies were carried out to evaluate the effects of the combination (COMB) as compared with L-carnitine, acetyl-L-carnitine, and propionyl-L-carnitine singly administered on the performance of endurance athletes (Study 1) and subjects practising non agonistic, recreational physical exercise (Study 2).

STUDY 1

Population: 40 male healthy volunteers used to practice long-distance races (e.g. marathon) for at least four years.

Study design: randomized, double-blind, parallel, controlled versus placebo for a period of 45 days.

Inclusion Criteria:
sex: male
age: 20–40 years
body weight: not exceeding 10% above normal body weight
Respiratory exchange rate: 0.8

Exclusion Criteria:
gastrointestinal, cardiovascular, skeletal muscle, and nervous system diseases
renal and hepatic insufficiency During the study, all subjects did not undergo unusual physical and nutritional stress.

Treatment

All subjects were orally administered 6 tablets per day (2×3, after meals) to warrant study blindness. Study design was maintained by varying the number of active tablets vs placebo tablets for each group of treatment, depending on the specific substance to be administered, as follows:

COMB was administered at the dosage of 1.5 g/day (3×500 mg tablet composed of LC 167 mg, PLC 167 mg, and ALC 167 mg, +3 placebo tablets) for 45 days in 8 subjects;

L-Carnitine (LC) was administered at the dosage of 2 g/day (4×500 mg tablet+2 placebo tablets) for 45 days in 8 subjects;

Propionyl-L-carnitine (PLC) was administered at the dosage of 2.5 g/day (5×500 mg tablet+1 placebo tablet) for 45 days in 8 subjects;

Acetyl-L-carnitine (ALC) was administered at the dosage of 3 g/day (6×500 mg tablet) for 45 days in 8 subjects;

Placebo (PLA, 6 tablets) was administered for 45 days in 8 subjects.

During the study, the athletes were requested to keep their training distance per week relatively constant.

Evaluation of Efficacy:

Oxygen consumption $VO_2$, ml/min) and peak treadmill running speed (km/h) were recorded for each athlete after completing a progressive treadmill test (0° gradient) until exhaustion. Athletes started running at 8 km/h and the running speed was increased every three minutes by 2 km/h until 16 km/h was reached.

Thereafter, the speed was increased every two minutes by 1 km/h until physical exhaustion which was measured according to the following two criteria: 1—stabilization in $VO_2$; 2—respiratory exchange ratio exceeding 1.1. Peak treadmill running speed was measured as the highest running speed the athlete was able to maintain for 60 seconds during the exercise test.

All subjects were evaluated at baseline ($T_0$) and at 45 days ($T_{45}$) after treatment. Moreover, hematochemical and urinary parameters were determined to monitor adverse events.

The data were analysed using the analysis of variance (ANOVA) including the factors subject, period and treatment. Differences in scores between the treatment groups were assessed using Student's t-test. Significance was established at $p<0.05$.

Results

Physical characteristics of athletes were: age (years) 27.5±3.8; height (cm) 175±6.5; body weight (kg) 69.9±7.

Results concerning the efficacy parameters were as follows:

At $T_{45}$, in the COMB group, peak running speed was significantly higher than that in the all other groups, while it was not associated with an increase of $VO_2$.

It is therefore apparent that treatment with COMB positively affects physical performance in endurance athletes.

No adverse events were reported.

STUDY 2

Population: 40 healthy volunteers (23 male e 17 female), practicing non agonistic, recreational physical exercise.

Study design: randomized, double-blind, parallel, controlled versus placebo for a period of 15 days.

Inclusion Criteria:
sex: male and female
age: 18–40 years
body weight: not exceeding 10% above normal body weight
Respiratory exchange rate: 0.8

Exclusion Criteria:
gastrointestinal, cardiovascular, skeletal muscle, and nervous system diseases
renal and hepatic insufficiency During the study, all subjects did not undergo unusual physical and nutritional stress.

Treatment

All subjects were orally administered 6 tablets per day (2×3, after meals) to warrant study blindness. Study design was maintained by varying the number of active tablets vs placebo tablets for each group of treatment, depending on the specific substance to be administered, as follows:

COMB was administered at the dosage of 1.5 g/day (3×500 mg tablet of LC 167 mg, PLC 167 mg, and ALC 167 mg, +3 placebo tablets) for 15 days in 8 subjects;

L-Carnitine (LC) was administered at the dosage of 2 g/day (4×500 mg tablet +2 placebo tablets) for 15 days in 8 subjects;

Propionyl-L-carnitine (PLC) was administered at the dosage of 2.5 g/day (5×500 mg tablet +1 placebo tablet) for 15 days in 8 subjects;

Acetyl-L-carnitine (ALC) was administered at the dosage of 3 g/day (6×500 mg tablet) for 15 days in 8 subjects;

Placebo (PLA, 6 tablets) was administered for 15 days in 8 subjects.

Evaluation of Efficacy:

| GROUP (n = 8) | Peak running speed (km/h) | | $VO_2$ (ml/min) | |
|---|---|---|---|---|
| | $T_0$ | $T_{45}$ | $T_0$ | $T_{45}$ |
| PLA | 19.7 ± 0.7 | 20.1 ± 0.8 | 3108.7 ± 325.4 | 3071.2 ± 245.4 |
| COMB | 19.6 ± 0.7 | 23.0 ± 0.7*$°^ | 3025.0 ± 110.2 | 2551.2 ± 146.5*°^ |
| LC | 19.5 ± 0.9 | 21.4 ± 0.7*° | 2916.2 ± 166.7 | 2850.0 ± 119.5 |
| ALC | 19.6 ± 0.7 | 20.0 ± 0.7^ | 2950.6 ± 96.0 | 2685.0 ± 105.1* |
| PLC | 19.6 ± 0.7 | 21.5 ± 0.5* | 2953.1 ± 97.3 | 2907.5 ± 115.0 |

Data are mean ± SD
*p < 0.05 vs PLA
$ p < 0.05 vs LC
° p < 0.05 vs ALC
^ p < 0.05 vs PLC At $T_0$, there were no statistically significant differences between treatment groups.

Maximal oxygen consumption ($VO_2$ max, ml/kg/min) and total work load (kgm/h) were measured to evaluate treatment efficacy.

At baseline ($T_0$) and at 15 days after treatment ($T_{15}$), all the included subjects underwent maximal ergospirometric effort test (triangular treadmill) with a work load according to the Bruce protocol (7 steps every 3 minutes, 10–22% inclination, 1.7–6.5 Mph speed).

Moreover, hematochemical and urinary parameters were determined to monitor adverse events.

The data were analysed using the analysis of variance (ANOVA) including the factors subject, period and treatment. Differences in scores between the treatment groups were assessed using Student's t-test. Significance was established at $p<0.05$.

Results

Physical characteristics of subjects were: age (years) 29±5.1; body weight (kg) 74±5.2; height (cm) 174.5±6.8.

Results concerning the efficacy parameters were as follows:

|  | Total work load (kgm/h) |  | VO₂ max (ml/kg/min) |  |
|---|---|---|---|---|
| GROUP (n = 8) | $T_0$ | $T_{15}$ | $T_0$ | $T_{15}$ |
| PLA | 9600.9 ± 1600.4 | 9800.4 ± 910.0 | 62.1 ± 4.9 | 61.8 ± 4.4 |
| COMB | 10390.2 ± 1400.5 | 13280.5 ± 700.1*$° | 61.5 ± 4.3 | 75.9 ± 3.3*$°^ |
| LC | 10200.5 ± 1510.1 | 11400.2 ± 700.2* | 60.6 ± 4.2 | 67.5 ± 2.5 |
| ALC | 10020.5 ± 1500.2 | 11100.4 ± 1100.8 | 61.7 ± 5.1 | 64.4 ± 4.9 |
| PLC | 10800.2 ± 10015.9 | 12100 ± 900.4* | 62.6 ± 4.8 | 69.0 ± 3.0* |

Data are mean ± SD
*$p < 0.05$ vs PLA
$ $p < 0.05$ vs LC
° $p < 0.05$ vs ALC
^ $p < 0.05$ vs PLC At $T_0$, there were no statistically significant differences between groups.

At $T_{45}$, in the COMB group, the total work load was significantly higher than that in the PLA, LC, and ALC groups. Moreover, $VO_2$ max was significantly higher than that in all the other groups. Consequently, subjects treated with COMB had a more efficient physical performance.

No adverse events were reported.

Effect of the Combination in Asthenic Individuals

The purpose of the study was to evaluate the effects of the combination (COMB) as compared with L-carnitine, acetyl-L-carnitine, and propionyl-L-carnitine singly administered in asthenic individuals.

The study was designed as a randomized, double-blind, parallel-group comparison between COMB and L-carnitine or acetyl-L-carnitine or propionyl-L-carnitine or placebo for a period of 30 days.

Subjects of either sex between the ages of 18 and 60 years suffering from asthenia following surgery (n=19) and infectious disease (n=15), and "idiopathic" asthenia (n=26) were elegible for inclusion. The exclusion criteria included history of cardiovascular, skeletal muscle and nervous system diseases, renal and hepatic insufficiency, and depression (diagnosed using the Beck depression scale).

The informed consent was obtained from all elegible subjects prior to the beginning of the trial.

Treatment

All subjects were administered 6 tablets per day (2×3, after meals) to warrant study blindness. Study design was maintained by varying the number of active tablets vs placebo tablets for each group of treatment, depending on the specific substance to be administered, as follows:

COMB was administered at the dosage of 1.5 g/day (3×500 mg tablet of LC 167 mg, PLC 167 mg, and ALC 167 mg, +3 placebo tablets) for 30 days in 12 subjects;

L-Carnitine (LC) was administered at the dosage of 2 g/day (4×500 mg tablet +2 placebo tablets) for 30 days in 12 subjects;

Propionyl-L-carnitine (PLC) was administered at the dosage of 2.5 g/day (5×500 mg tablet +1 placebo tablet) for 30 days in 12 subjects;

Acetyl-L-carnitine (ALC) was administered at the dosage of 3 g/day (6×500 mg tablet) for 30 days in 12 subjects;

Placebo (PLA, 6 tablets) was administered for 30 days in 12 subjects.

Evaluation of efficacy: asthenia was measured at baseline ($T_0$) and after 30 days of treatment ($T_{30}$) by using a 20-items self-report scale (MFI-20 scale, Smets E. M. A. et al. J. Psychosomatic Res 39: 315–325, 1995; Br J Cancer 73: 241–245, 1996) which covers general expressions of fatigue, physical fatigue, reduced activity, reduced motivation, and mental fatigue. A total score between 20 and 40 indicates the absence of asthenia whereas a score greater than 40 (up to a maximum of 100) indicates asthenia of progressive severity.

The data were analysed using the analysis of variance (ANOVA). Differences in scores between the treatment groups were assessed using Student's t-test. Significance was established at $p<0.05$.

Results

The following results were obtained:

|  | MFI-20 scale score | |
|---|---|---|
| GROUP (n = 12) | $T_0$ | $T_{30}$ |
| PLA | 73.2 ± 2.5 | 74.0 ± 3.5 |
| COMB | 70.4 ± 4.1 | 24.2 ± 2.2*$°^ |
| LC | 75.2 ± 6.2 | 52.5 ± 4.7*°^ |
| ALC | 69.8 ± 7.1 | 39.4 ± 5.5* |
| PLC | 70.9 ± 6.0 | 65.2 ± 6.6* |

Data are mean ± SD
*$p < 0.05$ vs PLA $ $p < 0.05$ vs LC ° $p < 0.05$ vs ALC ^ $p < 0.05$ vs PLC At $T_0$, the treatment groups did not differ significantly.

At $T_{30}$, subjects from the COMB group recovered from asthenia. The lc, plc and alc groups had a mean score significantly lower than that in the placebo group, but an almost normal mean score value was reached by the alc group only.

What is claimed is:

1. A nutritional supplement which comprises a combination of:

(a) L-carnitine;

(b) acetyl L-carnitine;

(c) propionyl L-carnitine;
or the pharmacologically acceptable salts thereof, wherein the weight ratio (a):(b):(c) ranges from 1:1:1 to 1:0.1:0.1.

2. The nutritional supplement of claim 1 which further comprises:
(d) isovaleryl L-carnitine or a pharmacologically acceptable salt thereof,
wherein the weight ratio (a):(b):(c):(d) ranges from 1:1:1:1 to 1:0.1:0.1:0.1.

3. The nutritional supplement of claim 1 which further comprises an essential aminoacid or mixtures thereof.

4. The nutritional supplement of claim 3 wherein the essential aminoacid is selected from the group of the branched-chain aminoacids valine, leucine and isoleucine or mixtures thereof.

5. The nutritional supplement of claim 3, wherein the weight ratio between the combination of L-carnitine, acetyl L-carnitine, propionyl L-carnitine and the essential aminoacid or the mixture thereof ranges from 3:1 to 1:1.

6. The nutritional supplement of claims 3 which further comprises glutamine, L-glutamic acid, L-aspartic acid and L-asparagine.

7. The nutritional supplement of claim 1 which further comprises a creatine selected from creatine and phosphocreatine.

8. The nutritional supplement of claim 1 which comprises:
(i) from 40 to 60% by weight of a mixture of L-carnitine, acetyl L-carnitine and propionyl L-carnitine or the pharmacologically acceptable salts thereof;
(ii) from 10 to 15% by weight of valine; from 10 to 15% by weight of leucine; from 10 to 15% by weight of isoleucine; and
(iii) from 8 to 12% by weight of creatine or phosphocreatine.

9. The nutritional supplement of claim 8, which further comprises from 10 to 30% by weight of non-essential aminoacids.

10. The nutritional supplement of claim 1 wherein the pharmacologically acceptable salt is selected from the group comprising chloride; bromide; iodide; aspartate; acid aspartate; citrate; acid citrate; tartrate; phosphate; fumarate; acid fumarate; glycerophophate; glucosephosphate; lactate; maleate; acid maleate; orotate; oxalate; acid oxalate; sulphate; acid sulphate; trichloroacetate and methanesulfonate.

11. The nutritional supplement of claim 1, which comprises:

| Basic Active ingredients | daily dose |
| --- | --- |
| L-carnitine fumarate [(= 143 mg L-carnitine inner salt)] | 200 mg |
| Acetyl L-carnitine | 75 mg |
| Propionyl L-carnitine | 75 mg |

-continued

| Basic Active ingredients | daily dose |
| --- | --- |
| Branched-chain amino acids and non-essential amino acids | |
| Isoleucine | 50 mg |
| Leucine | 50 mg |
| Valine | 50 mg |
| Aspartic acid | 150 mg |
| Glutamic acid | 200 mg |
| Asparagine | 100 mg |
| Fosfocreatine | 50 mg |
| Vitamins | |
| Vitamin C | 250 mg |
| Mineral salts | |
| Disodium citrate [(= 7,8 mg Na)] | 40 mg |
| Monopotassium phosphate [(= 8,6 mg K)] | 30 mg |
| Calcium lactate [(= 20 mg Ca)] | 110 mg |
| Magnesium taurinate [(= 73,0 mg Mg)] | 820 mg |
| Total amount of active ingredients: | 2250 mg |
| Excipients | 2750 mg |
| Total weight | 5000 mg. |

12. A method of facilitating the adaptation of skeletal muscle in individuals undergoing a program of strenuous physical exercise, comprising:
administering to an individual in need thereof a nutritional supplement which comprises a combination of:
(a) L-carnitine;
(b) acetyl L-carnitine;
(c) propionyl L-carnitine;
or the pharmacologically acceptable salts thereof, wherein the weight ratio (a):(b):(c) ranges from 1:1:1 to 1:0.1:0.1.

13. The method of claim 12, which comprises administering of 500 mg/day of L-carnitine, 50–500 mg/day of acetyl L-carnitine and 50–500 mg/day of propionyl L-carnitine or an equivalent amount by weight of a pharmacologically acceptable salt thereof to the individual in need thereof.

14. A method of counteracting defatigation and weariness in asthenic individuals, comprising:
administering to an individual in need thereof a nutritional supplement which comprises a combination of:
(a) L-carnitine;
(b) acetyl L-carnitine;
(c) propionyl L-carnitine;
or the pharmacologically acceptable salts thereof, wherein the weight ratio (a):(b):(c) ranges from 1:1:1 to 1:0.1:0.1.

* * * * *